United States Patent [19]

Colborn

[11] Patent Number: 5,504,238
[45] Date of Patent: Apr. 2, 1996

[54] METHOD FOR MAKING DIARYL CARBONATE

[75] Inventor: Robert E. Colborn, Schenectady, N.Y.

[73] Assignee: General Electric Company, Schenectady, N.Y.

[21] Appl. No.: 369,454

[22] Filed: Jan. 6, 1995

[51] Int. Cl.$^6$ .................................. C07C 68/00
[52] U.S. Cl. .................................. 558/274
[58] Field of Search ........................... 558/274

[56] References Cited

PUBLICATIONS

Kandanarachchi et al., J. Chem. Soc. Chem. Commun., pp. 777–778 (1992).
Kandanarachchi et al., J. Am. Chem. Soc., 116, pp. 5592–5600 and pp. 5601–5606 (1994).
Narasimhamurthy et al., Tetrahedron Letters, 27, pp. 991–992 (1986).
Fieser, Louis F. and Mary Fieser; *Reagents for Organic Synthesis;* John Wiley and Sons: New York, 1967; pp. 511–514.

*Primary Examiner*—Johann Richter
*Assistant Examiner*—Michael G. Ambrose
*Attorney, Agent, or Firm*—William H. Pittman

[57] ABSTRACT

Diaryl carbonate is prepared by hydrolysis of a tetraaryl orthocarbonate in the presence of an acid catalyst. The tetraaryl orthocarbonate is synthesized by a reaction between carbon disulfide and a cuprous phenate; the cuprous phenate can be made from cuprous chloride and the corresponding alkali metal phenate. The process may be integrated with recycle of by-products.

7 Claims, No Drawings

METHOD FOR MAKING DIARYL CARBONATE

BACKGROUND OF THE INVENTION

The present invention relates to a method for making a diaryl carbonate, such as diphenyl carbonate, by effecting the hydrolysis of a tetraaryl orthocarbonate.

Methods for making polycarbonates are constantly being evaluated. The route to polycarbonates by the melt transesterification of a diaryl carbonate often provides a significant environmental advantage over the reaction of bisphenols with phosgene under interfacial reaction conditions. In addition, polycarbonates prepared by melt transesterification have low levels of contaminants such as sodium and halide ions, and are therefore particularly suitable for use in optical applications such as for the manufacture of compact disks.

However, manufacture of polycarbonates by melt transesterification of diaryl carbonate has not been extensively exploited on a commercial scale. One reason why it has not been used more extensively is that a satisfactory synthesis for diaryl carbonate has not been developed.

For example, one procedure for making diaryl carbonates is based on a low conversion, multi-step melt transesterification technique employing a dialkyl carbonate and a phenol Another method employs phosgene with a phenol. A third procedure involves the direct carbonylation of phenol requiring a Pd catalyst which is difficult to recycle. As a result, additional procedures for making diaryl carbonates are of interest.

The conversion of tetraaryl orthocarbonates to diaryl carbonates is disclosed in Kandanarachchi et al., *J. Chem. Soc.*, 1992, 777–778, and Kandanarachchi et al., *J. Am. Chem. Soc.*, 116, 5592–5600 and 5601–5606 (1994). The reaction of carbon disulfide with a cuprous phenate to form a tetraaryl orthocarbonate is also known; reference is made to Narasimhamurthy et al., *Tetrahedron Letters*, 27,991–992 (1986). However, an integrated process for converting phenols to diphenyl carbonates via tetraaryl orthocarbonates does not appear to be known.

SUMMARY OF THE INVENTION

In one of its aspects, the invention is a method for making a diaryl carbonate comprising:

contacting a cuprous aryloxide with carbon disulfide to form a tetraaryl orthocarbonate and hydrolyzing said tetraaryl orthocarbonate.

A further aspect is an integrated process for making diaryl carbonate comprising the steps of:

contacting an alkali metal aryloxide with a cuprous halide to form a mixture of cuprous aryloxide and alkali metal halide, adding carbon disulfide to said mixture to form a tetraaryl orthocarbonate and cuprous sulfide, recovering said tetraaryl orthocarbonate and said cuprous sulfide from the resulting residue, converting said alkali metal halide to alkali metal hydroxide, recycling said alkali metal hydroxide to form said alkali metal aryloxide, and hydrolyzing said tetraaryl orthocarbonate in an aqueous organic solvent solution in the presence of an acidic catalyst to produce said diaryl carbonate.

DETAILED DESCRIPTION; PREFERRED EMBODIMENTS

The term "aryloxide" is used herein in place of "phenate" to avoid confusion with the phenate species which consists of the salts of phenol, $C_6H_5OH$.

Alkali metal aryloxides which can be used in the practice of the invention to make cuprous aryloxide can be formed by the reaction between a hydroxyaromatic compound and an alkali metal source such as an alkali metal hydride or hydroxide. Suitable alkali metal sources include the hydrides and hydroxides of sodium, potassium, and lithium.

The hydroxyaromatic compounds which are useful include compounds having the formula AOH, wherein A is a $C_{6-13}$ aryl radical. Suitable hydroxyaromatic compounds include phenol, p-cresol and δ-naphthol. Thus, the diaryl carbonates which can be synthesized include those having the formula $(AO)_2C=O$, wherein A is as previously defined, and include diphenyl carbonate (which is usually preferred), di-p-cresyl carbonate and δ-naphthyl carbonate.

Cuprous aryloxide may be synthesized by the reaction between an organic solvent solution of an alkali metal aryloxide and a substantially equimolar amount of a cuprous halide, preferably cuprous chloride. As previously discussed, the alkali metal aryloxide can be made from an alkali metal source, preferably in an inert atmosphere such as nitrogen although the presence of oxygen and/or water can be tolerated. Organic solvents which can be used include acetonitrile. Temperatures in the range of about 20°–40° C. are typical.

The product of the reaction of cuprous halide with alkali metal aryloxide is a slurry of cuprous aryloxide and alkali metal halide. It is then combined, most often at a temperature in the range of about 20°–40° C., with carbon disulfide, preferably in a molar ratio of carbon disulfide to cuprous aryloxide of at least 1:4. Following the precipitation of black cuprous sulfide, base, such as an aqueous alkali metal hydroxide solution, can be added to facilitate the isolation of the tetraaryl orthocarbonate.

Recovery of the tetraaryl orthocarbonate can be achieved if desired by extraction with an organic solvent such as ethyl ether. The product may be purified by recrystallization or the like. However, recovery prior to conversion to diaryl carbonate is usually not necessary.

Hydrolysis of the tetraaryl orthocarbonate to the corresponding hydroxyaromatic compound and diaryl carbonate can be effected in aqueous solution in the presence of a water-soluble organic solvent and an acidic catalyst at a temperature in the range of about 15°–100° C. Catalysts which can be used include Bronsted acids, particularly ion exchange resins in the acid form. Among the resins which have been found to be particularly effective are macroreticular polystyrenesulfonic acid cation exchange resins. Organic solvents which can be employed include phenol and acetonitrile.

In the integrated process which is another aspect of the invention, the initial step is the above-described conversion of alkali metal aryloxide to cuprous aryloxide. The by-product alkali metal chloride may remain in admixture with the cuprous aryloxide during the reaction with carbon disulfide. It is then removed by dissolution in water and converted, usually by electrolysis, to alkali metal hydroxide and chlorine and the alkali metal hydroxide is recycled for reaction with further hydroxyaromatic compound to form alkali metal aryloxide to be used in the reaction with cuprous halide.

Other recycles are also possible. For example, the chlorine and cuprous sulfide may be recycled and interreacted to form cuprous chloride for reaction with the alkali metal aryloxide.

The invention is illustrated by the following examples. All parts are by weight unless otherwise indicated.

EXAMPLE 1

There was added under a nitrogen atmosphere, 0.24 gram (10 mmol.) of sodium hydride to a solution of 0.941 gram of phenol dissolved in 50 ml. of acetonitrile. An immediate reaction resulted in the generation of hydrogen gas. The reaction was allowed to proceed for about 15 minutes and 0.99 gram (10 mmol.) of cuprous chloride was added. A golden slurry of cuprous phenoxide and sodium chloride resulted. After about 15 minutes, 0.86 gram (11.3 mmol.) of carbon disulfide was added to the mixture. A black precipitate of cuprous sulfide formed immediately. After 30 minutes, the reaction was worked up by addition of 0.8 gram (20 mmol.) of sodium hydroxide in the form of a solution in 100 ml. of water. The resulting mixture was extracted with ethyl ether. After one recrystallization from 95% ethanol, there was obtained a 90% yield of tetraphenyl orthocarbonate. LC analysis at 254 nm absorption showed less than 0.8% contamination.

There was added, at 70° C., 4.08 grams of "Amberlyst 15", a macroreticular sulfonic acid cation exchange resin based on polystyrene, to a homogeneous mixture of 8.5 grams of phenol and 0.5 gram of water. There was added 0.808 gram (2.1 mmol.) of tetraphenyl orthocarbonate to the resulting aqueous solution. After 20 minutes, the resulting mixture was analyzed by gas chromatography. It was found that the tetraphenyl orthocarbonate had been completely converted to diphenyl carbonate. Analysis by LC and UV at 254 nm absorption further showed no starting material.

EXAMPLE 2

The above procedure is repeated except that hydrolysis of the tetraphenyl orthocarbonate is effected by adding to a solution of 10.5 grams of phenol in 4.0 ml. of 0.1N aqueous sulfuric acid. The reaction is complete within two hours. An excellent yield of diphenyl carbonate is obtained and no significant by-products are formed.

What is claimed is:

1. An integrated process for making diaryl carbonate comprising the steps of:

contacting an alkali metal aryloxide with a cuprous halide to form a mixture of cuprous aryloxide and alkali metal halide, adding carbon disulfide to said mixture to form a tetraaryl orthocarbonate and cuprous sulfide, recovering said tetraaryl orthocarbonate and said cuprous sulfide from the resulting residue, converting said alkali metal halide to alkali metal hydroxide, recycling said alkali metal hydroxide to form said alkali metal aryloxide, and hydrolyzing said tetraaryl orthocarbonate in an aqueous organic solvent solution in the presence of an acidic catalyst to produce said diaryl carbonate.

2. A method according to claim 1 wherein the cuprous halide is cuprous chloride.

3. A method according to claim 1 wherein the alkali metal aryloxide is sodium phenate.

4. A method according to claim 1 wherein the catalyst is a macroreticular polystyrenesulfonic acid cation exchange resin.

5. A method according to claim 1 wherein the molar ratio of carbon disulfide to cuprous aryloxide is at least 1:4.

6. A method according to claim 2 wherein the conversion of alkali metal chloride to alkali metal hydroxide is by electrolysis.

7. A method according to claim 6 wherein chlorine formed during said electrolysis and said cuprous sulfide are recycled for interreaction to form cuprous chloride.

* * * * *